(12) United States Patent
Hanummappa et al.

(10) Patent No.: US 7,049,427 B2
(45) Date of Patent: May 23, 2006

(54) GENETIC SEQUENCES ENCODING DOMINANT-NEGATIVE CHALCONE SYNTHASE AND USES THEREFORE

(75) Inventors: Mamatha Hanummappa, Kwangju (KR); Goh Choi, Kwangju (KR); Giltsu Choi, Kwangju (KR)

(73) Assignee: Korea Kumho Petrochemical Co., LTD, Seoul (KR)

( * ) Notice: Subject to any disclaimer, the term of this patent is extended or adjusted under 35 U.S.C. 154(b) by 574 days.

(21) Appl. No.: 10/224,493

(22) Filed: Aug. 21, 2002

(65) Prior Publication Data

US 2004/0038407 A1    Feb. 26, 2004

(51) Int. Cl.
   C12N 15/29    (2006.01)
   C12N 15/52    (2006.01)
   C12N 15/82    (2006.01)

(52) U.S. Cl. .................. 536/23.6; 536/23.1; 536/23.2; 800/298

(58) Field of Classification Search ............... 536/23.1, 536/23.2, 23.6; 435/320.1; 800/278, 282, 800/298
   See application file for complete search history.

(56) References Cited

OTHER PUBLICATIONS

Ferrer J. et al. Nature Structural Biology, Aug. 1999; vol. 6, No. 8, pp. 775-784.*
Suzuki K. et al. Molecular Breeding, 2000, vol. 6, pp. 239-246.*
GenBank Accession AB012923 Jan. 17, 2001.*
Crete et al, The Plant Journal 28(5), 2001, pp. 493-501, Graft transmission of induced and spontaneous post-transcriptional . . . .
Fagard et al, Plant Molecular Biology 43, 2000, pp. 285-293, Systemic silencing signal(s).
Ferrer et al, Nature Structural Biology, vol. 6, No. 8, Aug. 1999, pp. 775-784, Structure of chalcone synthase and the . . . .
Holton et al, The Plant Cell, vol. 7, Jul. 1995, pp. 1071-1083, Genetics and Biochemistry of Anthocyanin Biosynthesis.
Jorgensen et al, Plant Molecular Biology 31, 1996, pp. 957-973, Chalcone synthase cosuppression phenotypes in petunia flowers . . . .
Palauqui et al, The EMBO Journal, vol. 16, No. 15, 1997, pp. 4738-4745, Systemic acquired silencing: transgene-specific . . . .
Tanaka et al, Plant Cell Physiol. 39(11), 1998, pp. 1119-1126, Metabolic Engineering to Modify Flower Color.
Vaucheret et al, Journal of Cell Science 114, 2001, pp. 3083-3091, Post-transcriptional gene silencing in plants.
Voinnet al, NATURE, vol. 389, Oct. 9, 1997, p. 553, Systemic signalling in gene silencing.
Voinnet et al, CELL, vol. 95, Oct. 16, 1998, pp. 177-187, Systemic Spread of Sequence-Specific Transgene RNA Degradation in . . . .

* cited by examiner

*Primary Examiner*—Russell P. Kallis
(74) *Attorney, Agent, or Firm*—Jacobson Holman PLLC

(57) ABSTRACT

The invention includes modified *Mazus* chalcone synthase (CHS) nucleic acids, which encode a modified chalcone synthase that has alanine instead of cysteine at the $165^{th}$ amino acid of *Mazus* CHS and either glycine or lysine instead of methionine at the $138^{th}$ amino acid of *Mazus* CHS. The property of the encoded modified *Mazus* CHS is characterized by its dominant-negative inhibition of CHS. The invention also includes plants having at least one cell expressing the modified *Mazus* CHS. Such plants are characterized by the decreased content of anthocyanins. The invention also includes vectors comprising at least a portion of the modified *Mazus* CHS nucleic acids. The invention also includes methods using such vectors for producing plants having the decreased content of anthocyanins.

4 Claims, 5 Drawing Sheets

A
```
              138                              165
    alf   GVDMPGADYQLTKLLGLRPYVKRYMMYQQGCFA
   arab   GVDMPGADYQLTKLLGLRPSVKRLMMYQQGCFA
    pet   GVDMPGCDYQLTKLLGLRPSVKRLMMYQQGCFA
   snap   GVDMPGADYQLTKLLGLRPSVKRFMMYQQGCFA
    tor   GVDMPGADYQLTKLLGLRPSVKRFMMYQQGCFA
  Mazus   GVDMPGADYQLTKLLGLRPSVKRFMMYQQGCFA mCHSG   ---G----------------------------A--
  mCHSK   ---K----------------------------A--
```

B

C

GENETIC SEQUENCES ENCODING DOMINANT-NEGATIVE CHALCONE SYNTHASE AND USES THEREFORE

FIELD OF THE INVENTION

The invention relates to modified *Mazus* CHS nucleic acids that encode modified CHS enzymes that inhibit CHS dominant-negatively and their uses for genetically altering plants to decrease the content of anthocyanins in the plants.

BACKGROUND OF THE INVENTION

Flower color is an important horticultural trait and is mainly produced by the flavonoid pigments, anthocyanins. Primarily produced to attract pollinators, flavonoids also protect the plant and its reproductive organs from UV damage, pests and pathogen (Brouillard and Cheminat, 1988; Gronquist et al., 2001). Classical breeding methods have been extensively used to develop cultivars with flowers varying in both the color and its intensity. The recent advance of knowledge on flower coloration at the biochemical and molecular level has made it possible to achieve this by genetic engineering (Tanaka et al., 1998).

Three different classes of anthocyanidins are responsible for the primary shade of flower color in many angiosperms: pelargonidin (orange to brick red), cyanidin (red to pink), and delphinidin (purple to blue). The anthocyanidin biosynthetic pathway is well established and most of the enzymes involved in the synthesis have been identified (FIG. 1) (Holton and Comish, 1995; Winkel-Shirley, 2001). It starts with the condensation of 4-coumaroyl-CoA and malonyl-CoA by chalcone synthase (CHS) to produce tetrahydroxychalcone. This is converted to a dihydroflavonol by the sequential action of chalcone isomerase (CHI) and flavanone 3-hydroxylase (F3H). The first produced dihydroflavonol is dihydrokaempferol (DHK). DHK is then converted either to kaempferol by flavonol synthase (FLS) or to leucopelargonidin by dihydroflavonol 4-reductase (DFR). Alternatively, DHK can be hydroxylated to dihydroquercetin (DHQ) or dihydromyricetin (DHM) by flavonoid 3'-hydroxylase (F3'H) or flavonoid 3'5'-hydroxylase (F3'5'H). DHQ and DHM are further converted to their respective flavonols (quercetin and myricetin) by FLS or may be reduced by DFR to yield leucoanthocyanidins (leucocyanidin and leucodelphinidin). The anthocyanidins that are synthesized from the leucoanthocyanidins by anthocyanidin synthase (ANS) are then glycosylated by flavonoid 3-O-glucosyl transferase (3GT) to produce anthocyanins. Further modification by rhamnosylation, methylation, or acylation results in a wide variety of anthocyanins (Kroon et al., 1994; Ronchi et al., 1995; Fujiwara et al., 1997; Yoshida et al., 2000; Yabuya et al., 2001). The spectral difference in flower color is mainly determined by the ratio of different classes of anthocyanins and other factors such as vacuolar pH, co-pigmentation, metal ion complexation and molecular stacking (Holton et al., 1993; Markham and Ofman, 1993; Mol et al., 1998; Tanaka et al., 1998; Aida et al., 2000). The final shade may be altered further by various factors including the shape of the epidermal cells or the presence of starch that gives creaminess (Markham and Ofman, 1993; Noda et al., 1994; Mol et al., 1998; van Houwelingen et al., 1998).

Genetic engineering to alter flower color has been attempted using various genes. Some species lack a particular color due to the absence of a biosynthetic gene or the substrate specificity of an enzyme in the pathway. For example, carnation lacks blue/purple colored flowers due to the absence of F3'5'H, while petunia lacks orange and brick-red flowers due to the inability of its DFR to reduce DHK (Gerats et al., 1982; Forkmann and Ruhnau, 1987). Genetic engineering of blue/purple colored carnation was achieved by introducing petunia F3'5'H gene and orange-colored petunia was developed by introducing DFR from other species (Meyer et al., 1987; Brugliera et al., 2000; Johnson et al., 2001). The modulation of color intensity has been another target for genetic engineering. Expression of biosynthetic genes such as CHS, F3H, and DFR in sense or antisense directions has been the most exploited method (van der Krol et al., 1990; Courtney-Gutterson et al., 1994; Jorgensen et al., 1996; Tanaka et al., 1998). The resulting sense suppression or antisense inhibition is collectively called post-transcriptional gene silencing (PTGS). Though these approaches have been fairly successful in the down-regulation of pigment synthesis, the necessity of cloning the gene of interest from a specific species or closely related species is the major drawback. Further, it is difficult to limit the PTGS to specific tissues (Palauqui et al., 1997; Voinnet and Baulcombe, 1997; Voinnet et al., 1998; Fagard and Vaucheret, 2000; Crete et al., 2001; Vaucheret et al., 2001). Alternatively, transcription factors that can either activate or repress the transcription of anthocyanin biosynthetic genes have been shown to be useful in regulating color intensity in model plants such as *Arabidopsis*, tobacco, and *Petunia* (Lloyd et al., 1992; Mol et al., 1998; Borevitz et al., 2000; Aharoni et al., 2001). The overexpression of transcription factors, however, generally alters the expression of many genes, thus the commercial viability of such transgenic flowers has yet to be determined (Lloyd et al., 1994; Bruce et al., 2000).

The biochemical and structural characterization of CHS suggests the possibility of designing a dominant-negative CHS that can be used to regulate flower color intensity. CHS is the first enzyme in the synthesis of various flavonoids including anthocyanins. It functions as a homodimer and carries out a series of reactions at a single active site (Tropf et al., 1995). The enzyme condenses a molecule of 4-coumaroyl-CoA with three of malonyl-CoA and folds the tetraketide intermediate into an aromatic ring structure (Schroder, 1999). Site-directed mutagenesis and inhibitor studies have identified the conserved cysteine and histidine residues that are important for the catalytic function of CHS (Lanz et al., 1991; Suh et al., 2000). The crystal structure of alfalfa CHS indicates that the conserved Cys164, Phe215, His303 and Asn336 form the catalytic active site (Ferrer et al., 1999). In addition, the crystal structure also shows that Met137 from the adjoining monomer extends into the cyclization pocket of CHS. This suggests that a CHS monomer requires the methionine from the adjoining monomer for its activity. Based on this structural information, we have generated CHS that has alanine instead of cysteine at the active site and either glycine or lysine instead of the methionine. The mutation of cysteine to alanine will result in the inactive form of CHS while the mutation of methionine to glycine or lysine will inactivate the function of an adjoining CHS if the methionine is really important as suggested by the crystal structure. Using transgenic *Arabidopsis*, we demonstrate that the mutated CHS is indeed dominant-negative. Our results confirm the importance of the methionine residue and demonstrate the utility of the dominant-negative CHS in modulating flower colour intensity even in a distantly related species.

Accordingly, the object of this invention is to provide modified *Mazus* CHS, which encodes a modified chalcone synthase that has alanine instead of cysteine at the $165^{th}$ amino acid of *Mazus* CHS and either glycine or lysine instead of methionine at the 138th amino acid of *Mazus* CHS.

It is also an object herein to provide transgenic plants expressing the modified Mazus CHS that confers a phenotype characterized by the decreased content of anthocyanins in the plants.

SUMMARY OF THE INVENTION

In accordance with the objects, the invention includes the modified *Mazus* CHS nucleic acids encoding the modified *Mazus* CHS that has alanine instead of cysteine at the 165th amino acid of *Mazus* CHS and either glycine or lysine instead of methionine at the 138th amino acid of *Mazus* CHS. The property of the modified CHS is characterized by its ability to inhibit CHS dominant-negatively.

The invention also includes plants having at least one cell transformed with a vector comprising at least a portion of the modified CHS nucleic acids. Such plants have a phenotype characterized by the decreased content of anthocyanins.

The invention also includes vectors capable of transforming a plant cell to decrease the content of anthocyanins.

The invention also includes methods for producing plants having the decreased content of anthocyanins. The methods includes steps of transforming plant cells with vectors containing the modified CHS gene; regenerating plants from the transformed cells and selecting the plant having the decreased content of anthocyanins.

DETAILED DESCRIPTION OF THE INVENTION

Cloning and Functional Characterization of *Mazus japonicus* CHS

Figure 1:
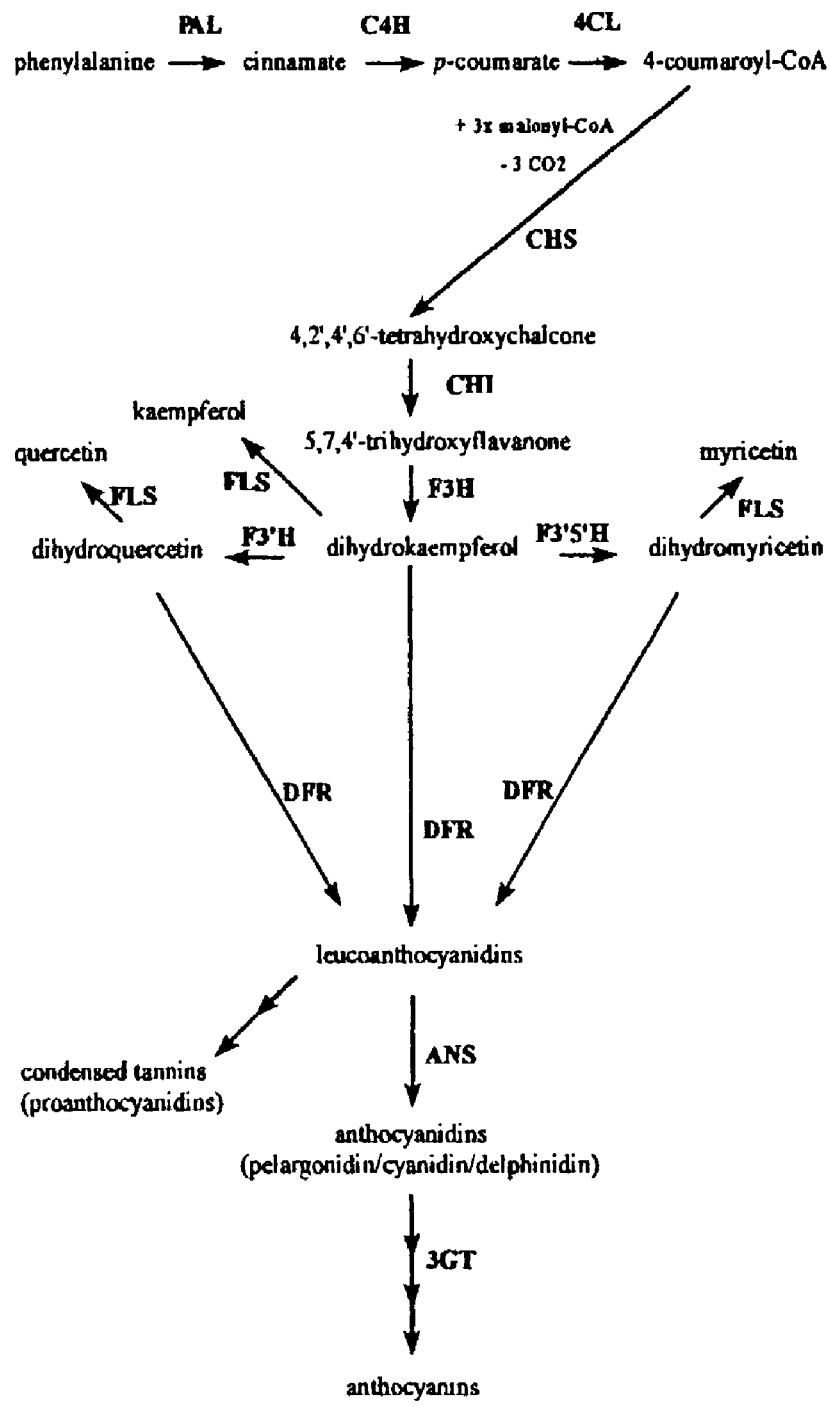
FIG. 1. General anthocyanin biosynthetic pathway showing major enzymes. PAL, phenylalanine ammonia lyase; C4H, cinnamic acid 4-hydroxylase; 4CL, 4-coumarate coenzyme A ligase; CHS, chalcone synthase; CHI, chalcone isomerase; F3H, flavanone 3-hydroxylase; FLS, flavonol synthase, F3'H, flavonoid 3' hydroxylase; F3'5'H, flavonoid 3'5' hydroxylase; DFR, dihydroflavonol4-reductase; ANS, anthocyanidin synthase; 3GT,3-O-Glucosyl transferase.
Figure 2:
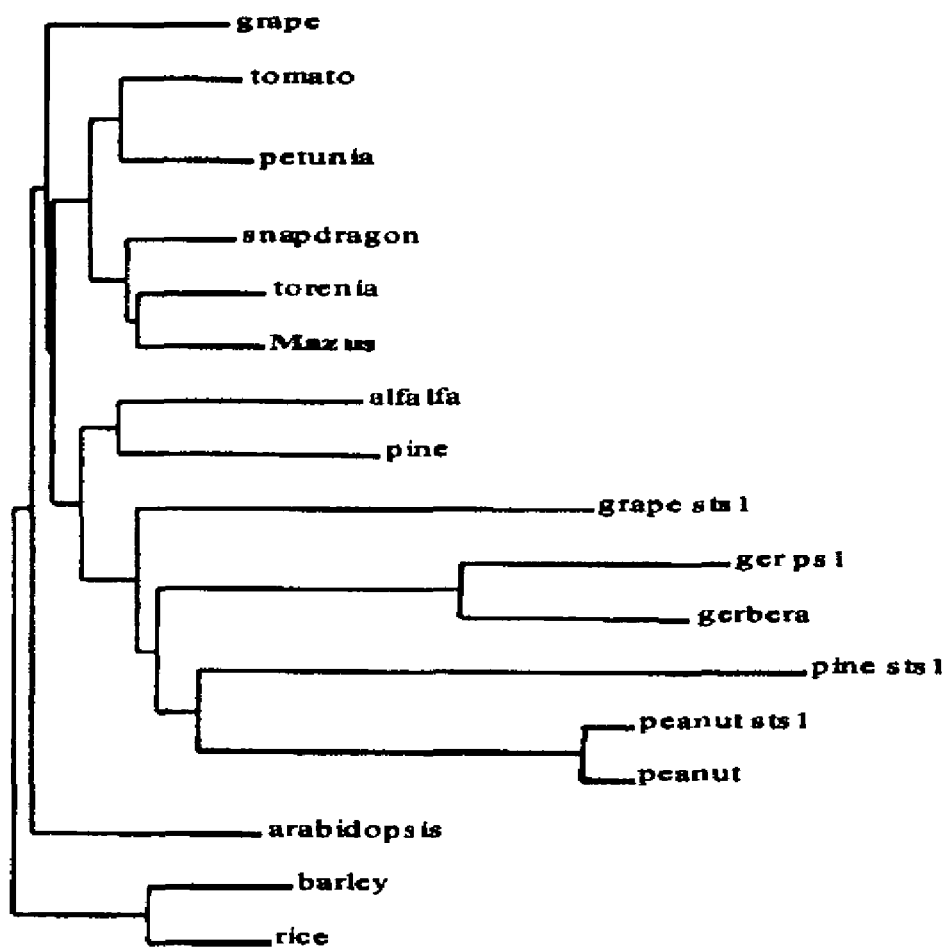
FIG. 2. Phylogenetic tree showing the homology between CHS from *Mazus* and other species. ger ps1, gerbera pyrone synthase 1; sts1, stilbene synthase 1.

A putative CHS was cloned from *Mazus japonicus*, a common garden plant belonging to Scrophulariaceae (Genbank accession no. AY131328). *Mazus* bears bilaterally symmetrical white flowers with lavender-shaded corolla tube. We have cloned the putative CHS gene as part of cloning all anthocyanin biosynthetic genes from Mazus. The phylogenetic analysis indicated that the putative CHS from *Mazus* is very similar to other known CHS enzymes, especially to snapdragon (*Antirrhinum majus*) and torenia (*Torenia hybrida*), which also belong to Scrophulariaceae (FIG. 2). Though it is likely that the gene encodes a real CHS, further experimental proof was required as stilbene synthase (STS) and other CHS-like enzymes do not branch separately in the phylogenetic tree (Tropf et al., 1994).

Figure 3:
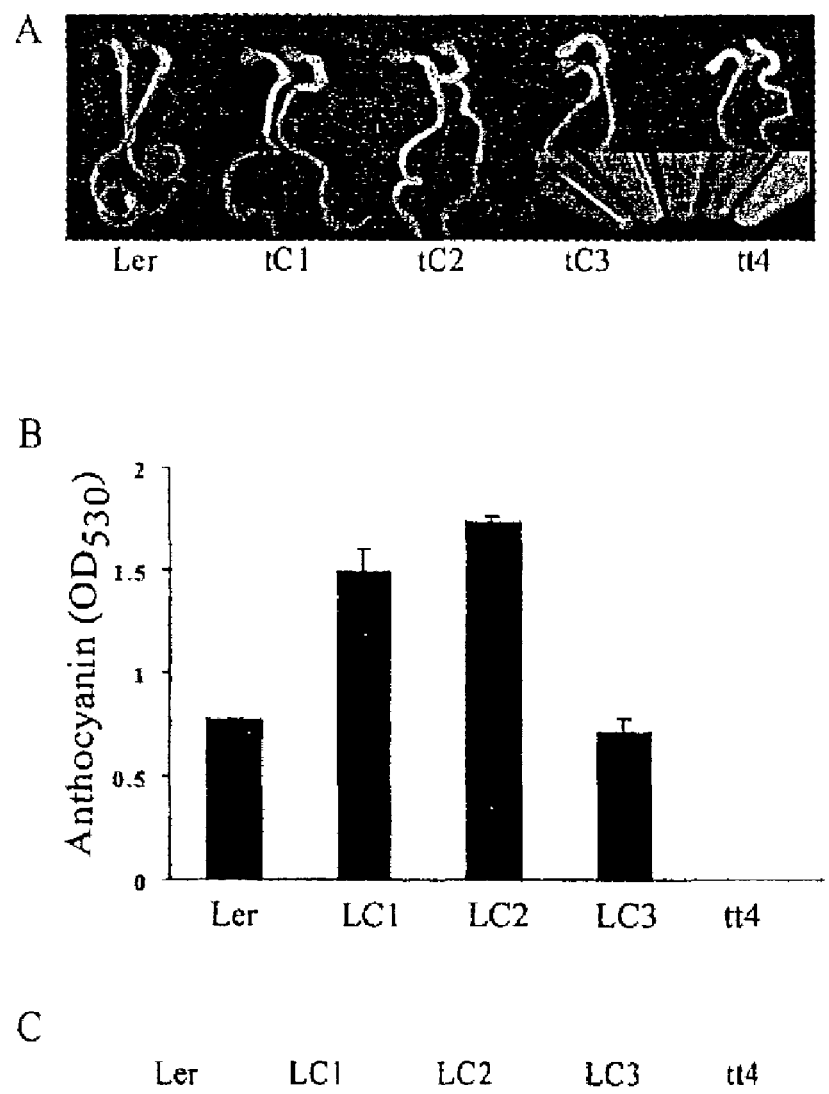
FIG. 3. Functional analysis of MjCHS in *Arabidopsis*. (A) MjCHS can rescue the yellow cotyledon and seed (inset) color of the CHS mutant tt4. tC1, 2 and 3 are independent homozygous lines of tt4 expressing CHS from Mazus. (B) Anthocyanin level in seedlings expressing CHS from Mazus. LC1, 2 and 3 represent independent homozygous transgenic lines. (C) MjCHS expression analysis in the overexpressor lines. MJCHS does not cross-hybridize with AtCHS and the lack of expression in LC3 corresponds to the anthocyanin level.

To determine if the putative CHS isolated from *Mazus* encodes a functional CHS, we expressed the gene both in the wild type *Arabidopsis* (Ler) and the chs mutant (tt4) backgrounds. Several independent homozygous lines were established and three lines of each were selected randomly for further analysis. To determine if the putative CHS can complement the tt4 mutation, we grew the seedlings on water agar plates containing 3% sucrose. As shown in FIG. 3A, wild type plants and all three transgenic lines expressing the putative CHS showed purple cotyledons while tt4 showed yellowish cotyledons. Consistently, both wild type and transgenic seeds showed brown coat color unlike yellow seed coat color of the tt4 mutant (FIG. 3A inset). The recovery of anthocyanin production in the transgenic lines indicated that the putative CHS from *Mazus* encodes a functional CHS. Henceforth, we refer to this gene as MjCHS.

The overexpression of maize CHS in *Arabidopsis* did not increase anthocyanin production (Dong et al., 2001). To test if the overexpression of MjCHS can increase anthocyanin in *Arabidopsis*, we grew both wild type and transgenic *Arabidopsis* plants on MS-agar plates containing 2% sucrose and quantitated anthocyanin content using a spectrophotometer. Two out of the three randomly chosen homozygous lines expressing MjCHS in Ler background accumulated more anthocyanin (FIG. 3B). To investigate if this increase reflects the expression of MjCHS, we did Northern analysis. As seen in FIG. 3C, the two lines that showed higher amount of anthocyanin expressed MJCHS, while the third line that showed similar amount as the wild type did not express the transgene. The results indicate that the overexpression of MjCHS can increase the anthocayanin levels in *Arabidopsis*. The contrasting result from the overexpression of maize CHS could be due to a subtle difference in the two CHS enzymes or different assay conditions used in the experiments.

Development of Two Dominant-Negative MjCHS

Figure 4:
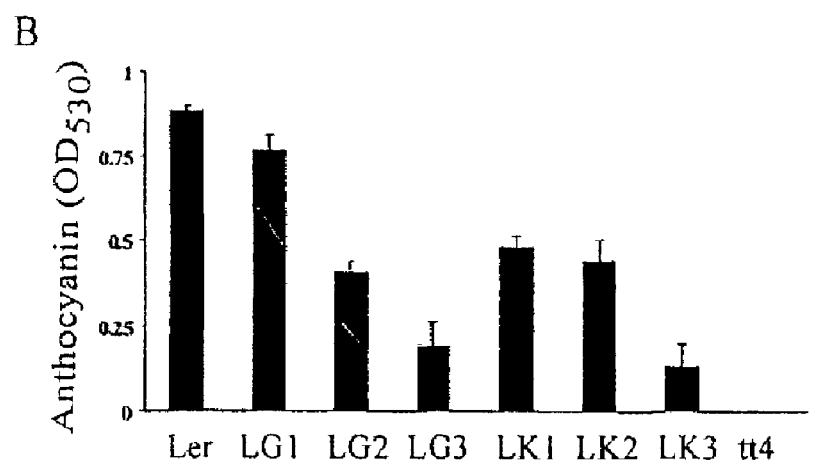
FIG. 4. Analysis of the dominant-negative lines. (A) Amino acid alignment of CHS showing the boxed residues Met138 which is predicted to be important for the function of the adjoining monomer and Cys165, shown to be the catalytic cysteine. Numbering is based on *Mazus* sequence. mCHSG and mCHSK represent the mutations induced. alg alfalfa (SEQ ID NO: 19); arab, *Arabidopsis thaliana* (SEQ ID NO: 20); pet, *petunia* (SEQ ID NO: 21); snap, snapdragon (SEQ ID NO: 22); tor, torenia (SEQ ID NO: 23). (B) Anthocyanin accumulation in seedlings of Ler expressing the dominant-negative MjCHS. (C) Endogenous CHS (AtCHS) (upper panel) and transgene (MjCHS) (;middle panel) expression in Ler and the dominant-negative lines. Lower panel shows the ribosomal RNA.
Figure 4:
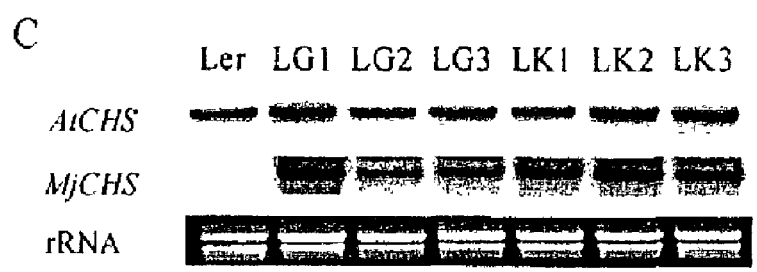

The crystal structure of alfalfa CHS suggests that a conserved methionine from a monomer is required for the function of an adjoining monomer (Ferrer et al., 1999). If this methionine is functionally important, the alteration of methionine to other amino acids will inhibit the function of the adjoining CHS, thus the mutation will be dominant-negative. To test this, we generated two mutated MjCHS genes by site-directed mutagenesis (FIG. 4A). One mutated MjCHS (mCHSG) has glycine instead of methionine at the 138$^{th}$ residue. Since glycine has a shorter side chain compared to that of methionine, the substrate-binding pocket of the adjoining monomer will be altered. The other mutated MjCHS (mCHSK) has lysine instead of methionine at the 138$^{th}$ residue. Since lysine is positively charged, the electrochemical property of the substrate-binding pocket of the adjoining monomer will be altered. To eliminate the catalytic activity of the mutated MjCHS, we also changed the catalytically important 165$^{th}$ cysteine to alanine. The mutation of this cysteine to either serine or alanine has been shown to inactivate the CHS (Lanz et al., 1991; Tropf et al., 1995; Jez et al., 2000).

To determine if the mutated MjCHS enzymes behave in a dominant-negative manner, we generated several transgenic Arabidopsis expressing the mutated mCHSG and mCHSK, and randomly chose three homozygous lines for further analysis. For the analysis, both wild type and the transgenic lines were grown on MS-agar plates containing 2% sucrose. Anthocyanin content was quantitated by a spectrophotometer (FIG. 4B). Both mCHSG and mCHSK transgenic lines showed reduced level of anthocyanin. This reduction was not due to the lower expression of endogenous Arabidopsis CHS in the transgenic lines (FIG. 4C).

Each monomer in a CHS dimmer can function independently and the inactivation of a monomer by mutating the cysteine residue does not affect the activity of adjoining monomer (Tropf et al., 1995). Therefore, the reduced anthocyanin level in the mCHSG and mCHSK transgenic lines indicates that the mutated MjCHS enzymes behave dominant-negatively. As a corollary, the methionine extending into the cyclization pocket of the dimerizing partner is functionally important for the activity of adjoining monomer. The dominant-negative action of both mCHSG and mCHSK further suggests that the alteration of substrate binding pocket either by changing the length of side chain or by changing the electrochemical property can inhibit CHS activity.

The degree of dominant-negativity depends on the amount of dominant-negative protein. Therefore, anthocyanin content in the transgenic plants is expected to be inversely correlated with the expression level of the mutated MjCHS enzymes. To test this hypothesis, we did a Northern analysis of MjCHS RNA. However, as shown in FIG. 4C, no correlation was detected. The variation in the anthocyanin level can be attributed to the actual amount of the mutant proteins translated. Alternatively, since different transgenic lines can have different tissue expression profiles of MjCHS, it is possible that the different levels of mutated MjCHS in the neck and cotyledon regions of transgenic seedlings, where the majority of anthocyanin is produced, are masked by the total MjCHS message.

Modulation of Flower Color by the Dominant-Negative MjCHS

Figure 5:
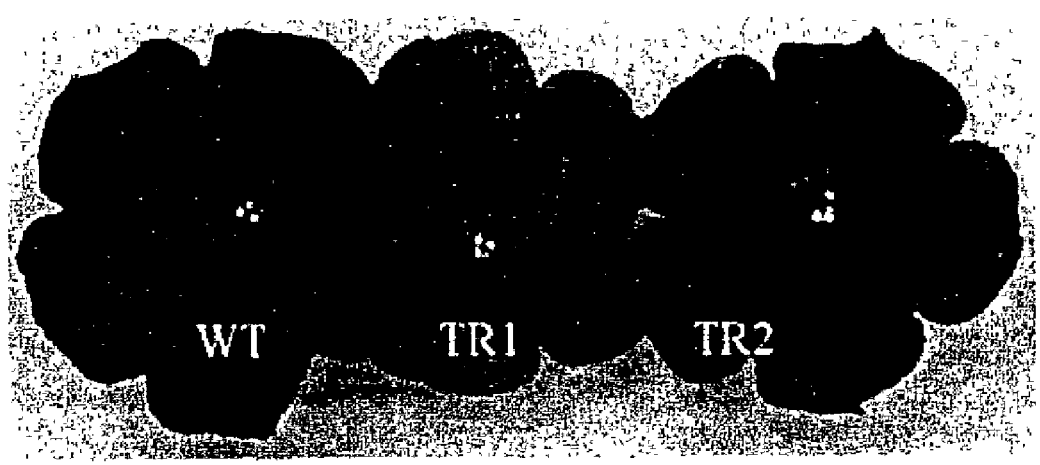
FIG. 5. Flower color intensity in transgenic petunia lines expressing a dominant-negative MjCHS (mCHSK). TR1 and TR2 represent independent transgenic lines. WT, wild type.

To further test if the dominant-negative MjCHS can be used to modulate the flower color intensity in a heterologous system, we transformed Petunia×hybrida cv Blue with mCHSK. Several transformants were obtained and all of them showed similar phenotype. As shown in FIG. 5, the petunia transformants expressing mCHSK showed reduced flower color intensity compared to wild type, indicating that the mutated MjCHS can also inhibit petunia CHS. Unlike the various color patterns observed in the sense suppression lines or antisense inhibition lines, all transgenic petunia lines expressing the dominant-negative CHS showed an even decrease of flower color intensity. The dominant-negative action of the mutated MjCHS enzymes depends on their ability to heterodimerize with the intrinsic CHS enzyme. The inhibition of anthocyanin production indicated that MjCHS can heterodimerize with both Arabidopsis and petunia CHS. The ability to regulate anthocyanin production in two different species suggests further utility of the dominant-negative MjCHS to modulate flower color intensity in many horticultural species.

The invention also provides plants having cells transformed with vectors comprising at least a portion of the modified Mazus CHS nucleic acids. Such plants have phenotypes characterized by the decreased content of anthocyanins specified by the modified CHSs. In the preferred embodiments, the invention provides plants having cells transformed with vectors comprising at least a portion of the modified Mazus CHS nucleic acids which encode modified chalcone synthase. Such plants have phenotypes characterized by the decreased content of anthocyanins. Plants that can be used to practice the invention include plants within the Division of Magnoliphyta, i.e. the angiosperms include the dicotyledons and the monocotyledons. The broad applicability of the modified CHS nucleic acids is based on the universal function of CHS enzyme in anthocyanin biosynthesis in divergent plant taxa. The parent plant used to practice the invention can be a wild type variant, a mutant which has been generated by the mutagenesis, or a transgenic line that has been generated by the recombinant techniques.

The invention also provides plant transformation vectors comprising at least a portion of the modified CHS nucleic acids.

The transformation of plants can be carried out in accordance with the invention by any of various transformation methods known to those skilled in the art of plant molecular biology. Particular methods for transformation include the transfer of nucleic acids into a plant cell by the microinjection, polyethylene glycol, electroporation, or microbombardment. Alternatively, plant cells can be transformed by Agrobacterium harboring vectors comprising at least a portion of modified CHS nucleic acids.

Regeneration of plants from the transformed cells can be carried out by any methods known to those skilled in the art. See, e.g., Methods in Enzymology, supra.; Methods in Enzymology, Vol 118; and Klee et al. Annual Review of Plant Physiology 38:467–486. Transformed cells or plants are selected based on their resistance to certain chemicals such as antibiotics or based on their phenotypes characterized by the decreased content of anthocyanins. The transformed plants can be self-fertilized or crossed with other plants. After the fertilization, the plants expressing at least portion of the modified CHS nucleic acids can be selected based on their resistance to certain chemicals such as antibiotics or based on their phenotypes characterized by the decreased content of anthocyanins. Alternatively, the transformed cells or a part of transformed plants can be grafted to other plants.

The following is presented as examples and is not to be construed as a limitation on the scope of the invention.

EXAMPLES

Cloning and Characterization of CHS from Mazus japonicus

A fragment of a putative CHS gene was cloned from Mazus japonicus, a common garden plant belonging to family Scrophulariaceae, using the degenerated primers (5'-TAYCARCARGCNTGYTTYGCNGG-3' (SEQ ID NO: 7), 5'-NAGDATNGCNGGNCCNC C-3' (SEQ ID NO: 8)). The full length CHS gene was cloned using the Marathon RACE kit with specific primers (5'-GTTGTCTGCTC-CGAGATCACT-3' (SEQ ID NO: 9) for 3' RACE, 5'-AGT-GATCTCGGAGCAGACAAC-3' (SEQ ID NO: 10) for 5' RACE) and the AP2 primer provided by the manufacturer (Clontech, Palo Alto, Calif., USA).

To determine if the putative CHS gene encodes a functional CHS, the gene was amplified with primers (5'-GAGATCTAGAAAAATGACGCCGACCGTCGAGGAG-3' (SEQ ID NO: 11) and 5'-GAGATCTAGATCAATTCATGAAGGGCACACT-3' (SEQ ID NO: 12)) and the amplified product cut with XbaI was cloned into the XbaI site of the GUS-deleted pBI121 vector. The gene cloned into the vector was introduced into *Agrobacterium* strain GV3101 and transformed into *Arabidopsis* wild type Landsberg *erecta* (Ler) or the tt4 mutant. Of the several independent homozygous lines established, three lines were chosen randomly for further analysis.

To determine the ability of the putative CHS to complement the tt4 mutation, we grew the transgenic tt4 lines for 5 days on water agar plates containing 3% sucrose (0.05% MES, 0.8% phytoagar, 3% sucrose, pH 5.7).

Construction and Characterization of Dominant Negative CHS

The full length MjCHS was cloned into pTOPOII vector. To mutate the cysteine at the 165th residue to alanine (Cys165Ala), we amplified the MjCHS in pTOPOII with Pfu polymerase using appropriate primer set (5'-TTCGC-CCGCGGGACGGTCCTC-3' (SEQ ID NO: 13), 5'-AG-CACCCTGCTGGTACATCAT-3' (SEQ ID NO: 14)). The amplified product was phosphorylated by polynucleotide kinase and ligated by T4 DNA ligase. The ligated product was transformed into *E.coli*. The mutated clone was confirmed by sequencing. To mutate the 138th methionine to either lysine (mCHSK) or glycine (mCHSG) together with Cys165Ala mutation, we amplified the Cys165Ala mutated CHS clone in pTOPOII with either K-primer set (5'-CCCG-GTGCCGACTACCAGCTC-3' (SEQ ID NO: 15), 5'-CT-TGTCGACCCCGCTGGTGGT-3' (SEQ ID NO: 16)) or G-primer set (5'-CCCGGTGCCGACTACCAGCTC-3' (SEQ ID NO: 17), 5'-GCCGTCGACCCCGCTGGTG GT-3' (SEQ ID NO: 18)). The amplified products were phosphorylated by polynucleotide kinase and ligated by T4 DNA ligase. The mutated genes were sequenced to confirm the mutations. The mutated full length MjCHS genes were cloned into the binary vector and introduced into *Arabidopsis*. The homozygous lines were renumbered after quantitating anthocyanin.

Quantitation of Anthocyanin

To determine anthocyanin levels in the transgenic plants, cold-imbibed seeds were sown on MS-agar plates containing 2% sucrose (1×MS salts, 0.05% MES, 0.8% phytoagar, 2% sucrose, pH 5.7) and grown for 5 days under continuous white light (2 mW/cm$^2$). The quantitation was done as described before (Shirley et al., 1995). Briefly, fifty seedlings were picked and soaked in 0.5 ml of the extraction solution (100% Methanol+0.5% HCl) overnight at 4° C. Next morning, the samples were briefly centrifuged and the solution was used for the spectrophotometric assay. Anthocyanin was quantitated by absorbance at $OD_{530}$. The $OD_{530}$ values of samples were subtracted with the $OD_{530}$ value of tt4 as an indicator of anthocyanin content. The experiment was triplicated.

Northern Analysis

Northern analysis was done as described before (Shin et al., 2002). Briefly, total RNA was extracted from 5 day old seedlings grown on the MS-agar plates containing 2% sucrose under continuous white light as for the anthocyanin extraction. Fifteen μg of total RNA was loaded into each lane and transferred to a Nylon membrane. The membrane was probed with $^{32}$P-labelled *Arabidopsis* full length CHS or *Mazus* full length CHS.

Petunia Transformation

*Petunia* (*Petunia×hybrida* cv Blue) was transformed with vector containing mCHSK gene as described by Johnson et al. (1999). Transformants were grown on soil until flowering. As control, transformants having the vector alone were generated and grown side by side.

What is claimed is:

1. An isolated *Mazus* chalcone synthase nucleic acid of SEQ ID NO: 1 encoding a chalcone synthase of SEQ ID NO: 2.

2. A modified chalcone synthase nucleic acid encoding a modified chalcone synthase, wherein the modified chalcone synthase comprises a Mazus chalcone synthase of SEQ ID NO: 2 having a substitution of any amino acid for CYS165 and a substitution of any amino acid for MET138.

3. The modified chalcone synthase nucleic acid of claim 2 encoding the modified chalcone synthase of SEQ ID NO: 4, wherein an alanine is substituted for CYS165 and a glycine is substituted for MET138.

4. The modified chalcone synthase nucleic acid of claim 2 encoding the modified chalcone synthase of SEQ ID NO: 6, wherein an alanine is substituted for CYS165 and a lysine is substituted for MET138.

* * * * *

SEQUENCE LISTING

<160> NUMBER OF SEQ ID NOS: 18

<210> SEQ ID NO 1
<211> LENGTH: 1179
<212> TYPE: DNA
<213> ORGANISM: Mazus japonicus

<400> SEQUENCE: 1

```
atgacgccga ccgtcgagga gattcgtagg gctcaacgtg ccgaggggcc ggccaccgtt    60
ttggcgatcg ggaccgcgac gccgtcgaac tgcgtcgatc agagcactta ccccgactac   120
tattttcgta tcacgaatag tgaacacatg actgatctta aagaaaaatt caagcgcatg   180
tgcgagaaat cgtacatcaa gaagcggtac atgcacctga ccgaagaaat cctgaaagaa   240
aacccgaaca tgtgtgcgta catggcccct tccctcgacg cgcgtcagga catcgttgtc   300
gtcgagatcc cgaagctcgg caaggaagcg gcccagaagg ccatcaagga atggggccag   360
cccaagtcca agatcaccca cctcgtcttc tgcaccacca gcggggtcga catgcccggt   420
```

-continued

```
gccgactacc agctcaccaa gctgctcggc cttcgcccct ccgtcaagcg cttcatgatg    480
taccagcagg gttgcttcgc cggcgggacg gtcctccgca tggccaagga ccttgcggag    540
aacaatgccg gtgccagggt ccttgttgtc tgctccgaga tcactgcagt tacgttccgt    600
ggcccgagcg atagccatct cgatagcctt gtcggccagg cgctgttcgg cgatggagct    660
gctgcggtca tcgtgggatc ggatccgatt gtgggagtcg agcgaccgtt gttccagatt    720
gtgtcggctg cccagacttt gctgccggat agtcacgggg cgatcgacgg tcacctccgt    780
gaagtagggc tcacctttca cctcctcaaa gatgttcccg ggctcatctc caaacacatc    840
gagaagagtc tcaaggaggc tttcgaccca ttgggcatct ccgactggaa ctccatcttc    900
tggatagccc atcccggtgg accggcaatc ctcgaccagg tcgagtccgt gttggccctg    960
aagcccgaaa gatgcgcgc cacgaggcag gtgcttagcg attatggcaa catgtcgagc    1020
gcatgcgtgc tgtttatact cgacgagatg aggaaggcgt cggcgaagga agggatgggg    1080
tctaccggag aaggcctcga ctggggcgtg ctgttcgggt tcgggccggg cctgaccgtg    1140
gagacggtgg tgctgcatag tgtgcccttc atgaattga                           1179
```

<210> SEQ ID NO 2
<211> LENGTH: 392
<212> TYPE: PRT
<213> ORGANISM: Mazus japonicus

<400> SEQUENCE: 2

```
Met Thr Pro Thr Val Glu Glu Ile Arg Arg Ala Gln Arg Ala Glu Gly
 1               5                  10                  15

Pro Ala Thr Val Leu Ala Ile Gly Thr Ala Thr Pro Ser Asn Cys Val
             20                  25                  30

Asp Gln Ser Thr Tyr Pro Asp Tyr Tyr Phe Arg Ile Thr Asn Ser Glu
         35                  40                  45

His Met Thr Asp Leu Lys Glu Lys Phe Lys Arg Met Cys Glu Lys Ser
     50                  55                  60

Tyr Ile Lys Lys Arg Tyr Met His Leu Thr Glu Glu Ile Leu Lys Glu
 65                  70                  75                  80

Asn Pro Asn Met Cys Ala Tyr Met Ala Pro Ser Leu Asp Ala Arg Gln
                 85                  90                  95

Asp Ile Val Val Val Glu Ile Pro Lys Leu Gly Lys Glu Ala Ala Gln
            100                 105                 110

Lys Ala Ile Lys Glu Trp Gly Gln Pro Lys Ser Lys Ile Thr His Leu
        115                 120                 125

Val Phe Cys Thr Thr Ser Gly Val Asp Met Pro Gly Ala Asp Tyr Gln
    130                 135                 140

Leu Thr Lys Leu Leu Gly Leu Arg Pro Ser Val Lys Arg Phe Met Met
145                 150                 155                 160

Tyr Gln Gln Gly Cys Phe Ala Gly Gly Thr Val Leu Arg Met Ala Lys
                165                 170                 175

Asp Leu Ala Glu Asn Asn Ala Gly Ala Arg Val Leu Val Val Cys Ser
            180                 185                 190

Glu Ile Thr Ala Val Thr Phe Arg Gly Pro Ser Asp Ser His Leu Asp
        195                 200                 205

Ser Leu Val Gly Gln Ala Leu Phe Gly Asp Gly Ala Ala Ala Val Ile
    210                 215                 220

Val Gly Ser Asp Pro Ile Val Gly Val Glu Arg Pro Leu Phe Gln Ile
225                 230                 235                 240
```

```
Val Ser Ala Ala Gln Thr Leu Leu Pro Asp Ser His Gly Ala Ile Asp
                245                 250                 255

Gly His Leu Arg Glu Val Gly Leu Thr Phe His Leu Leu Lys Asp Val
            260                 265                 270

Pro Gly Leu Ile Ser Lys His Ile Glu Lys Ser Leu Lys Glu Ala Phe
        275                 280                 285

Asp Pro Leu Gly Ile Ser Asp Trp Asn Ser Ile Phe Trp Ile Ala His
    290                 295                 300

Pro Gly Gly Pro Ala Ile Leu Asp Gln Val Glu Ser Val Leu Ala Leu
305                 310                 315                 320

Lys Pro Glu Lys Met Arg Ala Thr Arg Gln Val Leu Ser Asp Tyr Gly
                325                 330                 335

Asn Met Ser Ser Ala Cys Val Leu Phe Ile Leu Asp Glu Met Arg Lys
            340                 345                 350

Ala Ser Ala Lys Glu Gly Met Gly Ser Thr Gly Glu Gly Leu Asp Trp
        355                 360                 365

Gly Val Leu Phe Gly Phe Gly Pro Gly Leu Thr Val Glu Thr Val Val
    370                 375                 380

Leu His Ser Val Pro Phe Met Asn
385                 390

<210> SEQ ID NO 3
<211> LENGTH: 1179
<212> TYPE: DNA
<213> ORGANISM: Mazus japonicus

<400> SEQUENCE: 3
atgacgccga ccgtcgagga gattcgtagg gctcaacgtg ccgaggggcc ggccaccgtt      60
ttggcgatcg ggaccgcgac gccgtcgaac tgcgtcgatc agagcactta ccccgactac    120
tattttcgta tcacgaatag tgaacacatg actgatctta agaaaaaatt caagcgcatg    180
tgcgagaaat cgtacatcaa gaagcggtac atgcacctga ccgaagaaat cctgaaagaa    240
aacccgaaca tgtgtgcgta catggcccct tccctcgacg cgcgtcagga catcgttgtc    300
gtcgagatcc cgaagctcgg caaggaagcg gcccagaagg ccatcaagga atggggccag    360
cccaagtcca agatcaccca cctcgtcttc tgcaccacca gcggggtcga cggcccggt     420 gccgactacc agctcaccaa gctgctcggc cttcgcccct ccgtcaagcg cttcatgatg    480
taccagcagg gtgctttcgc cggcgggacg gtcctccgca tggccaagga ccttgcggag    540
aacaatgccg gtgccagggt ccttgttgtc tgctccgaga tcactgcagt tacgttccgt    600
ggcccgagcg atagccatct cgatagcctt gtcggccagg cgctgttcgg cgatggagct    660
gctgcggtca tcgtgggatc ggatccgatt gtgggagtcg agcgaccgtt gttccagatt    720
gtgtcggctg cccagacttt gctgccggat agtcacgggg cgatcgacgg tcacctccgt    780
gaagtagggc tcacctttca cctcctcaaa gatgttcccg gctcatctc  caaacacatc    840 gagaagagtc tcaaggaggc tttcgaccca ttgggcatct ccgactggaa ctccatcttc    900
tggatagccc atcccggtgg accggcaatc ctcgaccagg tcgagtccgt gttggccctg    960
aagcccgaaa agatgcgcgc cacgaggcag gtgcttagcg attatggcaa catgtcgagc   1020
gcatgcgtgc tgtttatact cgacgagatg aggaaggcgt cggcgaagga agggatgggg   1080
tctaccggag aaggcctcga ctggggcgtg ctgttcgggt tcgggccggg cctgaccgtg   1140
gagacggtgg tgctgcatag tgtgcccttc atgaattga                           1179
```

```
<210> SEQ ID NO 4
<211> LENGTH: 392
<212> TYPE: PRT
<213> ORGANISM: Mazus japonicus

<400> SEQUENCE: 4
```

| | | | | | | | | | | | | | | | |
|---|---|---|---|---|---|---|---|---|---|---|---|---|---|---|---|
| Met | Thr | Pro | Thr | Val | Glu | Glu | Ile | Arg | Arg | Ala | Gln | Arg | Ala | Glu | Gly |
| 1 | | | | 5 | | | | | 10 | | | | | 15 | |
| Pro | Ala | Thr | Val | Leu | Ala | Ile | Gly | Thr | Ala | Thr | Pro | Ser | Asn | Cys | Val |
| | | | 20 | | | | | 25 | | | | | 30 | | |
| Asp | Gln | Ser | Thr | Tyr | Pro | Asp | Tyr | Tyr | Phe | Arg | Ile | Thr | Asn | Ser | Glu |
| | | | 35 | | | | | 40 | | | | | 45 | | |
| His | Met | Thr | Asp | Leu | Lys | Glu | Lys | Phe | Lys | Arg | Met | Cys | Glu | Lys | Ser |
| | 50 | | | | | 55 | | | | | 60 | | | | |
| Tyr | Ile | Lys | Lys | Arg | Tyr | Met | His | Leu | Thr | Glu | Ile | Leu | Lys | Glu |
| 65 | | | | | 70 | | | | | 75 | | | | | 80 |
| Asn | Pro | Asn | Met | Cys | Ala | Tyr | Met | Ala | Pro | Ser | Leu | Asp | Ala | Arg | Gln |
| | | | | 85 | | | | | 90 | | | | | 95 | |
| Asp | Ile | Val | Val | Glu | Ile | Pro | Lys | Leu | Gly | Lys | Glu | Ala | Ala | Gln |
| | | | | 100 | | | | | 105 | | | | | 110 | |
| Lys | Ala | Ile | Lys | Glu | Trp | Gly | Gln | Pro | Lys | Ser | Lys | Ile | Thr | His | Leu |
| | | | 115 | | | | | 120 | | | | | 125 | | |
| Val | Phe | Cys | Thr | Thr | Ser | Gly | Val | Asp | Gly | Pro | Gly | Ala | Asp | Tyr | Gln |
| | 130 | | | | | 135 | | | | | 140 | | | | |
| Leu | Thr | Lys | Leu | Leu | Gly | Leu | Arg | Pro | Ser | Val | Lys | Arg | Phe | Met | Met |
| 145 | | | | | 150 | | | | | 155 | | | | | 160 |
| Tyr | Gln | Gln | Gly | Ala | Phe | Ala | Gly | Gly | Thr | Val | Leu | Arg | Met | Ala | Lys |
| | | | | 165 | | | | | 170 | | | | | 175 | |
| Asp | Leu | Ala | Glu | Asn | Asn | Ala | Gly | Ala | Arg | Val | Leu | Val | Val | Cys | Ser |
| | | | 180 | | | | | 185 | | | | | 190 | | |
| Glu | Ile | Thr | Ala | Val | Thr | Phe | Arg | Gly | Pro | Ser | Asp | Ser | His | Leu | Asp |
| | | | 195 | | | | | 200 | | | | | 205 | | |
| Ser | Leu | Val | Gly | Gln | Ala | Leu | Phe | Gly | Asp | Gly | Ala | Ala | Ala | Val | Ile |
| | 210 | | | | | 215 | | | | | 220 | | | | |
| Val | Gly | Ser | Asp | Pro | Ile | Val | Gly | Val | Glu | Arg | Pro | Leu | Phe | Gln | Ile |
| 225 | | | | | 230 | | | | | 235 | | | | | 240 |
| Val | Ser | Ala | Ala | Gln | Thr | Leu | Leu | Pro | Asp | Ser | His | Gly | Ala | Ile | Asp |
| | | | | 245 | | | | | 250 | | | | | 255 | |
| Gly | His | Leu | Arg | Glu | Val | Gly | Leu | Thr | Phe | His | Leu | Leu | Lys | Asp | Val |
| | | | 260 | | | | | 265 | | | | | 270 | | |
| Pro | Gly | Leu | Ile | Ser | Lys | His | Ile | Glu | Lys | Ser | Leu | Lys | Glu | Ala | Phe |
| | | | 275 | | | | | 280 | | | | | 285 | | |
| Asp | Pro | Leu | Gly | Ile | Ser | Asp | Trp | Asn | Ser | Ile | Phe | Trp | Ile | Ala | His |
| | 290 | | | | | 295 | | | | | 300 | | | | |
| Pro | Gly | Gly | Pro | Ala | Ile | Leu | Asp | Gln | Val | Glu | Ser | Val | Leu | Ala | Leu |
| 305 | | | | | 310 | | | | | 315 | | | | | 320 |
| Lys | Pro | Glu | Lys | Met | Arg | Ala | Thr | Arg | Gln | Val | Leu | Ser | Asp | Tyr | Gly |
| | | | | 325 | | | | | 330 | | | | | 335 | |
| Asn | Met | Ser | Ser | Ala | Cys | Val | Leu | Phe | Ile | Leu | Asp | Glu | Met | Arg | Lys |
| | | | 340 | | | | | 345 | | | | | 350 | | |
| Ala | Ser | Ala | Lys | Glu | Gly | Met | Gly | Ser | Thr | Gly | Glu | Gly | Leu | Asp | Trp |
| | | | 355 | | | | | 360 | | | | | 365 | | |
| Gly | Val | Leu | Phe | Gly | Phe | Gly | Pro | Gly | Leu | Thr | Val | Glu | Thr | Val | Val |
| 370 | | | | | 375 | | | | | 380 | | | | | |

Leu His Ser Val Pro Phe Met Asn
385                 390

<210> SEQ ID NO 5
<211> LENGTH: 1179
<212> TYPE: DNA
<213> ORGANISM: Mazus japonicus

<400> SEQUENCE: 5

```
atgacgccga ccgtcgagga gattcgtagg gctcaacgtg ccgaggggcc ggccaccgtt       60
ttggcgatcg ggaccgcgac gccgtcgaac tgcgtcgatc agagcactta ccccgactac      120
tattttcgta tcacgaatag tgaacacatg actgatctta agaaaaatt caagcgcatg       180
tgcgagaaat cgtacatcaa gaagcggtac atgcacctga ccgaagaaat cctgaaagaa      240
aacccgaaca tgtgtgcgta catggcccct ccctcgacg cgcgtcagga catcgttgtc       300
gtcgagatcc cgaagctcgg caaggaagcg gcccagaagg ccatcaagga atggggccag      360
cccaagtcca agatcaccca cctcgtcttc tgcaccacca gcggggtcga caagcccggt      420
gccgactacc agctcaccaa gctgctcggc cttcgcccct ccgtcaagcg cttcatgatg      480
taccagcagg gtgctttcgc cggcgggacg gtcctccgca tggccaagga ccttgcggag      540
aacaatgccg gtgccagggt ccttgttgtc tgctccgaga tcactgcagt tacgttccgt      600
ggcccgagcg atagccatct cgatagcctt gtcggccagg cgctgttcgg cgatggagct      660
gctgcggtca tcgtgggatc ggatccgatt gtgggagtcg agcgaccgtt gttccagatt      720
gtgtcggctg cccagacttt gctgccggat agtcacgggg cgatcgacgg tcacctccgt      780
gaagtagggc tcacctttca cctcctcaaa gatgttcccg ggctcatctc caaacacatc      840
gagaagagtc tcaaggaggc tttcgaccca ttgggcatct ccgactggaa ctccatcttc      900
tggatagccc atcccggtgg accggcaatc ctcgaccagg tcgagtccgt gttggccctg      960
aagcccgaaa gatgcgcgc cacgaggcag gtgcttagcg attatggcaa catgtcgagc     1020
gcatgcgtgc tgtttatact cgacgagatg aggaaggcgt cggcgaagga agggatgggg     1080
tctaccggag aaggcctcga ctggggcgtg ctgttcgggt tcgggccggg cctgaccgtg     1140
gagacggtgg tgctgcatag tgtgcccttc atgaattga                            1179
```

<210> SEQ ID NO 6
<211> LENGTH: 392
<212> TYPE: PRT
<213> ORGANISM: Mazus japonicus

<400> SEQUENCE: 6

Met Thr Pro Thr Val Glu Glu Ile Arg Arg Ala Gln Arg Ala Glu Gly
1               5                   10                  15

Pro Ala Thr Val Leu Ala Ile Gly Thr Ala Thr Pro Ser Asn Cys Val
            20                  25                  30

Asp Gln Ser Thr Tyr Pro Asp Tyr Tyr Phe Arg Ile Thr Asn Ser Glu
        35                  40                  45

His Met Thr Asp Leu Lys Glu Lys Phe Lys Arg Met Cys Glu Lys Ser
    50                  55                  60

Tyr Ile Lys Lys Arg Tyr Met His Leu Thr Glu Glu Ile Leu Lys Glu
65                  70                  75                  80

Asn Pro Asn Met Cys Ala Tyr Met Ala Pro Ser Leu Asp Ala Arg Gln
                85                  90                  95

Asp Ile Val Val Val Glu Ile Pro Lys Leu Gly Lys Glu Ala Ala Gln
            100                 105                 110

-continued

```
Lys Ala Ile Lys Glu Trp Gly Gln Pro Lys Ser Lys Ile Thr His Leu
        115                 120                 125

Val Phe Cys Thr Thr Ser Gly Val Asp Lys Pro Gly Ala Asp Tyr Gln
        130                 135                 140

Leu Thr Lys Leu Leu Gly Leu Arg Pro Ser Val Lys Arg Phe Met Met
145                 150                 155                 160

Tyr Gln Gln Gly Ala Phe Ala Gly Gly Thr Val Leu Arg Met Ala Lys
                165                 170                 175

Asp Leu Ala Glu Asn Asn Ala Gly Ala Arg Val Leu Val Val Cys Ser
                180                 185                 190

Glu Ile Thr Ala Val Thr Phe Arg Gly Pro Ser Asp Ser His Leu Asp
                195                 200                 205

Ser Leu Val Gly Gln Ala Leu Phe Gly Asp Gly Ala Ala Val Ile
        210                 215                 220

Val Gly Ser Asp Pro Ile Val Gly Val Glu Arg Pro Leu Phe Gln Ile
225                 230                 235                 240

Val Ser Ala Ala Gln Thr Leu Leu Pro Asp Ser His Gly Ala Ile Asp
                245                 250                 255

Gly His Leu Arg Glu Val Gly Leu Thr Phe His Leu Leu Lys Asp Val
                260                 265                 270

Pro Gly Leu Ile Ser Lys His Ile Glu Lys Ser Leu Lys Glu Ala Phe
        275                 280                 285

Asp Pro Leu Gly Ile Ser Asp Trp Asn Ser Ile Phe Trp Ile Ala His
        290                 295                 300

Pro Gly Gly Pro Ala Ile Leu Asp Gln Val Glu Ser Val Leu Ala Leu
305                 310                 315                 320

Lys Pro Glu Lys Met Arg Ala Thr Arg Gln Val Leu Ser Asp Tyr Gly
                325                 330                 335

Asn Met Ser Ser Ala Cys Val Leu Phe Ile Leu Asp Glu Met Arg Lys
                340                 345                 350

Ala Ser Ala Lys Glu Gly Met Gly Ser Thr Gly Glu Gly Leu Asp Trp
        355                 360                 365

Gly Val Leu Phe Gly Phe Gly Pro Gly Leu Thr Val Glu Thr Val Val
        370                 375                 380

Leu His Ser Val Pro Phe Met Asn
385                 390

<210> SEQ ID NO 7
<211> LENGTH: 23
<212> TYPE: DNA
<213> ORGANISM: Mazus japonicus
<220> FEATURE:
<221> NAME/KEY: variation
<222> LOCATION: (3, 6, 9, 12, 15, 18, 21)
<223> OTHER INFORMATION: wherein y is pyrimidine, r is purine, and n is
      any nucleotide base.

<400> SEQUENCE: 7
taycarcarg cntgyttygc ngg                                            23

<210> SEQ ID NO 8
<211> LENGTH: 18
<212> TYPE: DNA
<213> ORGANISM: Mazus japonicus
<220> FEATURE:
<221> NAME/KEY: variation
<222> LOCATION: (1, 4, 7, 10, 13, 16)
<223> OTHER INFORMATION: wherein y is pyrimidine, r is purine, and n is
``` any nucleotide base, and d is not c.

<400> SEQUENCE: 8
nagdatngcn ggnccncc                                              18

<210> SEQ ID NO 9
<211> LENGTH: 21
<212> TYPE: DNA
<213> ORGANISM: Mazus japonicus

<400> SEQUENCE: 9
gttgtctgct ccgagatcac t                                          21

<210> SEQ ID NO 10
<211> LENGTH: 21
<212> TYPE: DNA
<213> ORGANISM: Mazus japonicus

<400> SEQUENCE: 10
agtgatctcg gagcagacaa c                                          21

<210> SEQ ID NO 11
<211> LENGTH: 34
<212> TYPE: DNA
<213> ORGANISM: Mazus japonicus

<400> SEQUENCE: 11
gagatctaga aaaatgacgc cgaccgtcga ggag                            34

<210> SEQ ID NO 12
<211> LENGTH: 31
<212> TYPE: DNA
<213> ORGANISM: Mazus japonicus

<400> SEQUENCE: 12
gagatctaga tcaattcatg aagggcacac t                               31

<210> SEQ ID NO 13
<211> LENGTH: 21
<212> TYPE: DNA
<213> ORGANISM: Mazus japonicus

<400> SEQUENCE: 13
ttcgcccgcg ggacggtcct c                                          21

<210> SEQ ID NO 14
<211> LENGTH: 21
<212> TYPE: DNA
<213> ORGANISM: Mazus japonicus

<400> SEQUENCE: 14
agcaccctgc tggtacatca t                                          21

<210> SEQ ID NO 15
<211> LENGTH: 21
<212> TYPE: DNA
<213> ORGANISM: Mazus japonicus

<400> SEQUENCE: 15
cccggtgccg actaccagct c                                          21

<210> SEQ ID NO 16
<211> LENGTH: 21

-continued

```
<212> TYPE: DNA
<213> ORGANISM: Mazus japonicus

<400> SEQUENCE: 16
cttgtcgacc ccgctggtgg t                                              21

<210> SEQ ID NO 17
<211> LENGTH: 21
<212> TYPE: DNA
<213> ORGANISM: Mazus japonicus

<400> SEQUENCE: 17
cccggtgccg actaccagct c                                              21

<210> SEQ ID NO 18
<211> LENGTH: 21
<212> TYPE: DNA
<213> ORGANISM: Mazus japonicus

<400> SEQUENCE: 18
gccgtcgacc ccgctggtgg t                                              21
```